United States Patent [19]

Lanari

[11] Patent Number: Plant 6,662

[45] Date of Patent: Mar. 14, 1989

[54] CARNATION NAMED LANARIC

[75] Inventor: Fernand Lanari, Cagnes-sur-Mer, France

[73] Assignee: Selecta Klemm K.G., Stuttgart, Fed. Rep. of Germany

[21] Appl. No.: 100,718

[22] Filed: Sep. 24, 1987

[51] Int. Cl.[4] ..... A01H 5/00

[52] U.S. Cl. ..... Plt./71

[58] Field of Search ..... Plt./70–71

*Primary Examiner*—Robert E. Bagwill

*Attorney, Agent, or Firm*—Charles W. Rummler

[57] ABSTRACT

A new variety of carnation plant particularly distinguished by its continuous year around production of medium sized blooms of a solid light pink coloration and by its many closely packed petals, the flowers being borne singly on strong, upright stems, which reach a height of about 50 to 60 cm. on a plant having a vigorous, upright growth habit.

1 Drawing Sheet

BACKGROUND OF THE NEW PLANT

This new carnation variety originated as a seedling of unknown parentage discovered by me among my collection of carnation varieties maintained for breeding purposes at Cagnes-Sur-Mer, France, this particular seedling having been selected by me for propagation and commercial exploitation because of the very charming form and coloration of its blooms. Asexual propagation of this new carnation variety was done under my direction by means of cuttings in the greenhouses of Selecta Klemm K.G. at Stuttgart, Muhlhausen, West Germany, with such success that propagation by means of cuttings was carried on through several successive generations, which demonstrated conclusively that the novel characteristics of my new plant would be carried on from generation to generation and appeared to be firmly fixed. This new plant is presently being propagated for commercial purposes in Italy and Israel, as well as Germany, and has appeared to have experienced material success in the commercial market.

DESCRIPTION OF THE DRAWING

My new carnation cultivar is illustrated by the accompanying photographic drawing, which shows the typical inflorescence on the stem of a fully grown plant, the view including buds and flowers, together with a face view of a fully opened blossom, and a specimen of the calyx with the sepals from which the flower petals have been removed. The colors shown are as close to those herein specified as is reasonably possible to obtain by professional photographic procedures.

DESCRIPTION OF THE NEW PLANT

The following is a detailed description of my new carnation cultivar based upon observations of plants grown under conventional greenhouse procedures at Stuttgart, West Germany, the color designations being according to The R.H.S. Colour Chart published by The Royal Horticultural Society of London, England.

THE PLANT

Origin: Seedling.

Parentage: A cross of unknown varieties grown in my collection of unnamed and unpatented carnation plants maintained for breeding purposes.

Classification:

*Botanic.*—*Dianthus caryophyllus.*

*Commercial.*—Dianthini.

Form: Bush.

Height: About 50 to 60 cm.

Growth: Vigorous and upright.

Branching: Normal.

Foliage:

*Quantity.*—Moderate.

*Number of leaves.*—About fourteen per stem.

*Leaf size.*—About 10 cm. long and 1 cm wide.

*Shape.*—Lanceolate with entire margins.

*Texture.*—Smooth.

*Color.*—Grey green on both upper and under sides.

THE BUD

Size: Medium.

*Diameter.*—About 12 mm.

*Length.*—About 20 mm.

Shape: Ovoid.

Opening rate: Moderate.

Color:

*When sepals first divide.*—Hot Pink-Blue.

*When petals begin to unfurl.*—Lavender.

Sepals:

*Character.*—Ovate with acuminate apex. The sepals are connected together at the calyx and extend upwardly with generally ovate form and and acute apex. The sepals stand up when the flowers open.

*Color.*—Grey Green on both inside and outside.

Calyx:

*Shape.*—Cylindrical.

*Size.*—Medium; about 12 mm. wide and 17 mm. long.

*Splitting.*—The calyx does not split.

*Aspect.*—Smooth.

Peduncle:

*Length.*—About 30 to 35 mm.

*Character.*—Erect and rigid.

*Color.*—Grey Green.

THE FLOWER

Blooming habit: Continuous the year around.

Size of bloom: Medium.

*Diameter.*—About 35 to 40 mm.

*Depth.*—About 35 mm.

Borne: Singly on strong, upright pedicels.

Shape: High Centered as bloom first opens and when bloom matures.

Petalage:

*Number of petals.*—As many as about fifty.

*Arrangement.*—Imbricated.

*Form.*—Fan-shaped with serrated margins.

*Texture.*—Soft.

*Color.*—Outer Petals: Body — RHS 74 D. Base — RSH 75 D. Reverse side — RHS 75 D. Inside Petals: Body — RHS 74 D. Base — RHS 74 D. Reverse side — RHS 74 D.

Peduncle:

*Length.*—About 30 to 35 cm.

*Color.*—Grey Green.

*Character.*—Sturdy and upright.

Persistence: The petals hang on and dry as the blooms stay upright.

Fragrance: Noticeable.

Lasting quality:

*On the plant.*—About twenty days.

*As a cut flower.*—About ten to fifteen days.

THE REPRODUCTIVE ORGANS

Stamens:

*Arrangement.*—General. Anthers and pollen are rarely present.

Pistils:

*Number.*—Three.

*Stigmas.*—Color: White.

Characteristics of ovary: The same as the carnation genus.

This new carnation seedling is a part of the dianthini group. It is stronger and more intensive than the variety 'Eolo' with bigger flowers and a better average quality. It is a heavy producer with at least two crops per year.

I claim:

1. The new and distinctive carnation and parts thereof of the dianthini group, substantially as herein shown and described, characterized by its year around productivity of clean, light pink flowers carried on rigid and erect pedicels and productive of two crops per year.

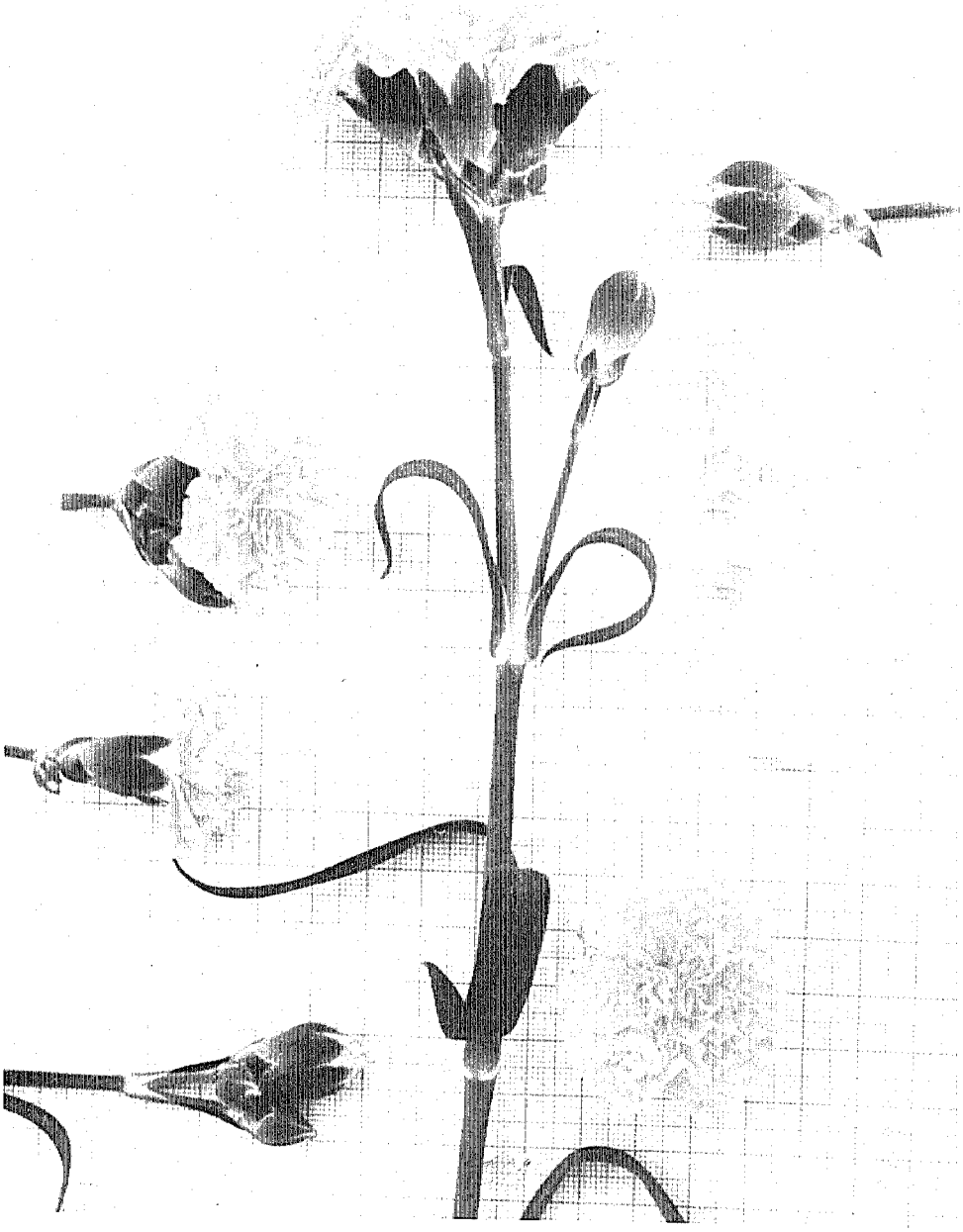

* * * * *